US006921898B1

(12) United States Patent
Chen

(10) Patent No.: US 6,921,898 B1
(45) Date of Patent: Jul. 26, 2005

(54) BI-DIRECTIONAL REFLECTANCE DISTRIBUTION FUNCTION DETERMINATION BY LARGE SCALE FIELD MEASUREMENT

(75) Inventor: Hsing-Cheng Chen, McLean, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 288 days.

(21) Appl. No.: 10/175,532

(22) Filed: Jun. 20, 2002

(51) Int. Cl.[7] ................................................ G01J 5/02
(52) U.S. Cl. ...................................................... 250/340
(58) Field of Search ........................................ 250/340

(56) References Cited

U.S. PATENT DOCUMENTS

| 3,515,462 | A | * | 6/1970 | Tomokazu et al. .......... 359/752 |
| 4,466,748 | A |   | 8/1984 | Needham |
| 4,611,929 | A | * | 9/1986 | Holyer ....................... 374/124 |
| 4,806,018 | A |   | 2/1989 | Falk |
| 5,315,513 | A |   | 5/1994 | Abreu et al. |
| 5,637,873 | A |   | 6/1997 | Davis et al. |
| 5,790,188 | A | * | 8/1998 | Sun ............................. 348/144 |
| 5,884,226 | A |   | 3/1999 | Anderson et al. |

OTHER PUBLICATIONS

P.K. Acharya, A. Berk, G.P. Anderson, N.F. Larsen, S–Chee Tsay and K.H. Stamnes, "MODTRAN4: Multiple Scattering and Bi–Directional Reflectance Distribution Function (BRDF) Upgrades to MODTRAN," *Society of Photo–Optical Instrumentation Engineers(SPIE) Proceedings*, Optical Spectroscopic Techniques and Instrumentation for Atmospheric and Space Research III, held Jul. 1999, Allen M. Larar, Ed., Oct. 1999, vol, 3756, pp 354–362.

Bruce W. Ball, "SYNSEA Code for Generating Synthetic IR Imagery of Sea," *Society of Photo–Optical Instrumentation Engineers(SPIE) Proceedings*, Characterization, Propagation, and Simulation of Sources and Backgrounds II, held Apr. 20, 1992, Orlando, Florida, Dieter Clement et al., Eds., Sep. 1992, vol. 1687, pp 289–298.

Reiner, Irving, *Introduction to Matrix Theory and Linear Algebra*, Holt Rinehart Winston, New York, 1971, entire book.

* cited by examiner

*Primary Examiner*—Constantine Hannaher
*Assistant Examiner*—Shun Lee
(74) *Attorney, Agent, or Firm*—Howard Kaiser

(57) ABSTRACT

Thermal images of an object are produced outdoors so as to be significantly differentiated temporally and/or geometrically and be inclusive of natural background such as would be illuminated by sunlight. A calibration of the thermal imager (e.g., radiometer) against theoretical blackbody radiation is effected using measured incident radiation, resulting in a calculated pixel intensity. A system transfer function calculation of the pixel intensity is effected, resulting in a radiance. A matrix inversion calculation of all of the radiances considered together is effected, resulting in a bi-directional reflectance distribution function (BRDF). Advantageously, the BRDF is determined from the target in a direct but mathematically-enhanced manner, thereby making economic use of natural illumination and obviating the need for modelling, simulating or reconstructing the target.

12 Claims, 13 Drawing Sheets

BI-DIRECTIONAL REFLECTANCE DISTRIBUTION FUNCTION DETERMINATION BY LARGE SCALE FIELD MEASUREMENT

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to methods and apparatuses for determining reflectance characteristics of objects, more particularly for determining the bi-directional reflectance distribution function characteristic of a target surface.

The Bi-directional Reflectance Distribution Function ("BRDF") is defined as the ratio of the differential scattered power to the differential incident power on a surface.

$$BRDF = \frac{dL_s(\theta_s, \phi_s)}{dE_i(\theta_i, \phi_i)} = \frac{P_s/\Omega A \cos\theta_s}{P_i/A} \quad (1)$$

The BRDF is typically measured using an apparatus which allows the sample to be illuminated with a collimated beam from a range of incident angles. A receiver, subtending a solid angle, can be positioned at a range of scatter directions. Alternatively, the relative radiance of the sample can be measured versus that of a standard characterized by a BRDF which is already known for the bi-directional geometry.

The U.S. Navy is interested in evaluating the BRDF of various types of coatings. The Coatings Engineering Evaluation Program ("CREEP") is a conventional computer model for computing the BRDF of a coating having plural layers (e.g., a multilayered paint coating). A CREEP code can compute the scattering by pigments and rough interfaces as well as the multiple reflections between layers. Generally, the energy is broken down by CREEP into a beam component (which is energy that has been attenuated but not scattered) and a diffuse component (which is energy that has been scattered at least once). Existing computer codes contained in CREEP have been used to calculate the BRDF of pigmented coatings having various particles of different sizes, shapes and densities embedded in a binder matrix. However, CREEP is limitedly useful in such applications, since CREEP calculations result only in qualitative answers.

The BRDFs of various target surfaces have been measured by the U.S. Navy using a SOC-200 bi-directional reflectometer manufactured by Surface Optics Corporation, 11555 Rancho Bernardo Road, San Diego, Calif., 92127, telephone number (858) 675-7404, fax number (858) 675-2028, website "Surface Optics Web," http://www.surfaceoptics.com/. Such reflectometric devices and techniques are limited in terms of size of the sample. For instance, the standard sample size for a Surface Optics Corp. SOC-200 is a one-inch diameter. Oversized samples of up to one-foot diameter can be accommodated, provided special care is taken. A notable disadvantage of this methodology is that the making of a sample without loss of the original information is not a trivial process. Furthermore, there are problems with light source and instrumentation stability, thus yielding highly variable results for identical samples.

SUMMARY OF THE INVENTION

In view of the foregoing, it is an object of the present invention to provide an efficient and reliable method for determining the bidirectional reflectance distribution function ("BRDF") of an object regardless of the object's size.

It is another object of the present invention to provide an efficient and reliable method for determining the BRDF of various kinds of coatings.

The present invention provides an analysis and imaging methodology for measuring the BRDF of any target surface. The inventive methodology involves the large scale field measurement of a target and its reflecting background in the thermal IR and visible regions. Typical embodiments of the present invention succeed in measuring the BRDF implicitly but directly from real targets of various sizes without going through the non-trivial process of making samples of certain sizes. Notable among the many applications of the present invention is the evaluation of various types of coatings. Inventive practice can determine numerically and experimentally the effects of various coating and substrate combinations, coating thicknesses and surface roughnesses on the BRDFs of selective targets.

In accordance with many embodiments of the present invention, a radiance-related physical property determination method comprises the steps of: generating plural distinguishable thermal images each being characterized by plural pixels; obtaining thermal values associated with the generating of the thermal images; obtaining pixel intensity values based on the obtained thermal values; and, obtaining radiance values based on the obtained pixel intensity values. According to usual inventive practice, the thermal images are geometrically distinguishable and/or temporally distinguishable. Typical inventive practice involves the calculation of one or more bi-directional reflectance distribution functions (BRDFs). According to such inventive embodiments, the present invention's radiance-related physical property determination method further comprises effecting mathematical matrix inversion to obtain a bidirectional reflectance distribution function from the obtained radiance values. Generally speaking, the more images generated, the more accurate the BRDF determinations. Additionally or alternatively, inventive practice sometimes involves the prediction of one or more target signatures and/or background signatures.

Generally, the inventively obtained BRDF information relates the differential scattered power to the differential incident power. This BRDF information can be used according to this invention to predict target signatures in the viewing geometries of all azimuth and elevation angles under various environmental conditions. The present invention provides for new techniques of target signature evaluation measurement, such as may be of interest to the U.S. Navy, wherein BRDF and background measurements are included. Further possible benefits of inventive practice include the modification of existing paint (e.g., on U.S. Navy ships and vehicles) for reducing target-background signature contrast and spatial variation of the target signature in order to improve the camouflage properties of military targets.

Advantageously, the present inventions measures the BRDF implicitly but directly a from real targets of various sizes without undertaking the significantly arduous procedures involving the making of samples of particular sizes. Furthermore, the present invention introduces a new methodology of effecting target signature evaluation measurements (such as may be of interest to the U.S. Navy) by including BRDF and background measurements. In addition, the present invention provides a very economical way of measuring the BRDF, because the natural background is the source of illumination in accordance with the present invention. Moreover, by measuring the wave band-averaged BRDF for immediate real applications, the present invention furthers convenience and practicality.

Other objects, advantages and features of this invention will become apparent from the following detailed description of the invention when considered in conjunction with the accompanying drawings.

BRIEF DESCRIPTION OF THE DRAWINGS

In order that the present invention may be clearly understood, it will now be described, by way of example, with reference to the accompanying drawings, wherein like numbers indicate the same or similar components, and wherein.

DETAILED DESCRIPTION OF THE INVENTION

Figure 1:
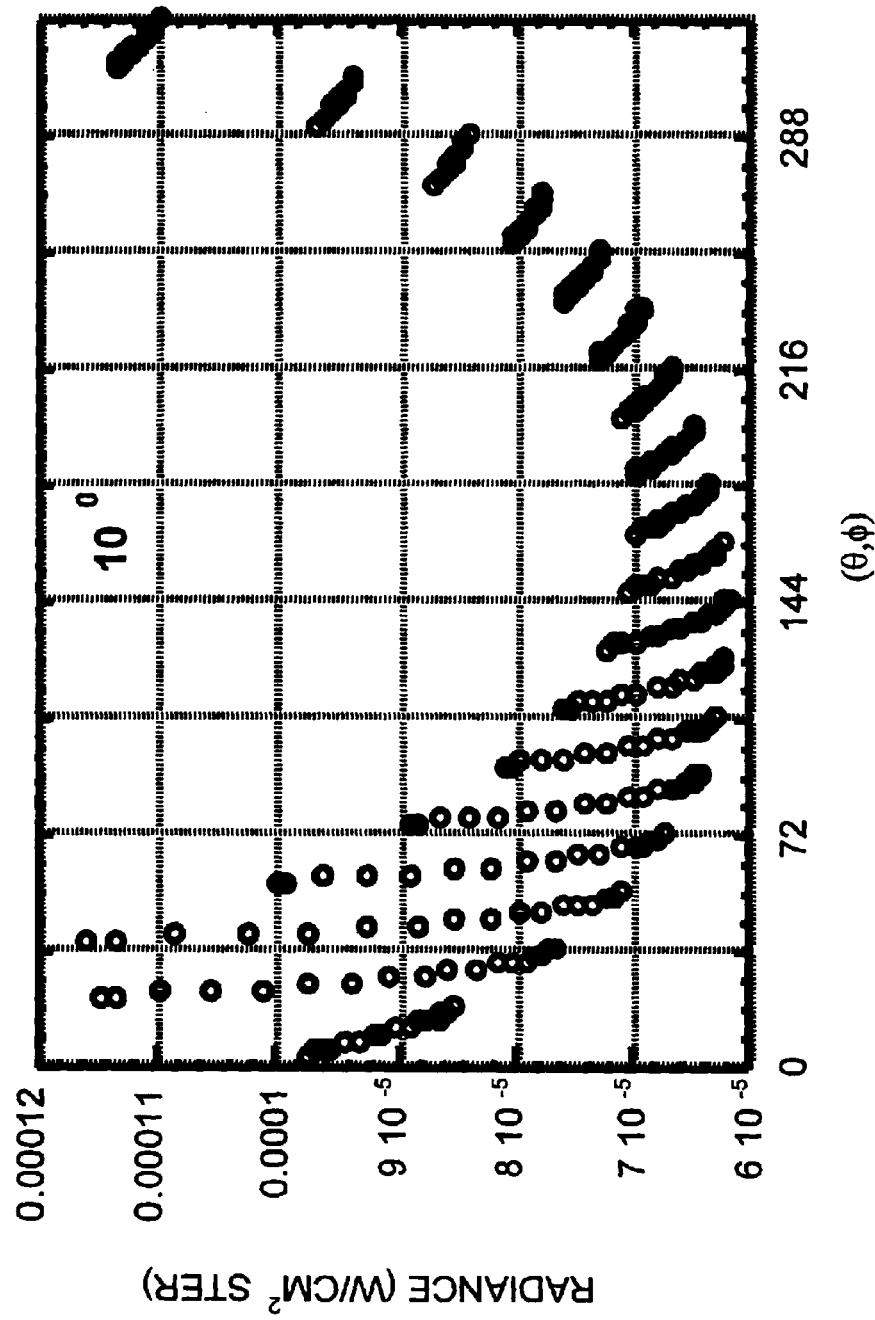
FIG. 1 through FIG. 8 are graphical representations of the typical sky radiance (3–5 µm) calculated from MODTRAN for the sun's zenith angle in ten degree increments from ten degrees to eighty degrees, in accordance with an embodiment of the present invention. The sun's zenith angle in FIG. 1, FIG. 2, FIG. 3, FIG. 4, FIG. 5, FIG. 6, FIG. 7 and FIG. 8 are 10°, 20°, 30°, 40°, 50°, 60°, 70° and 80°, respectively.
Figure 2:
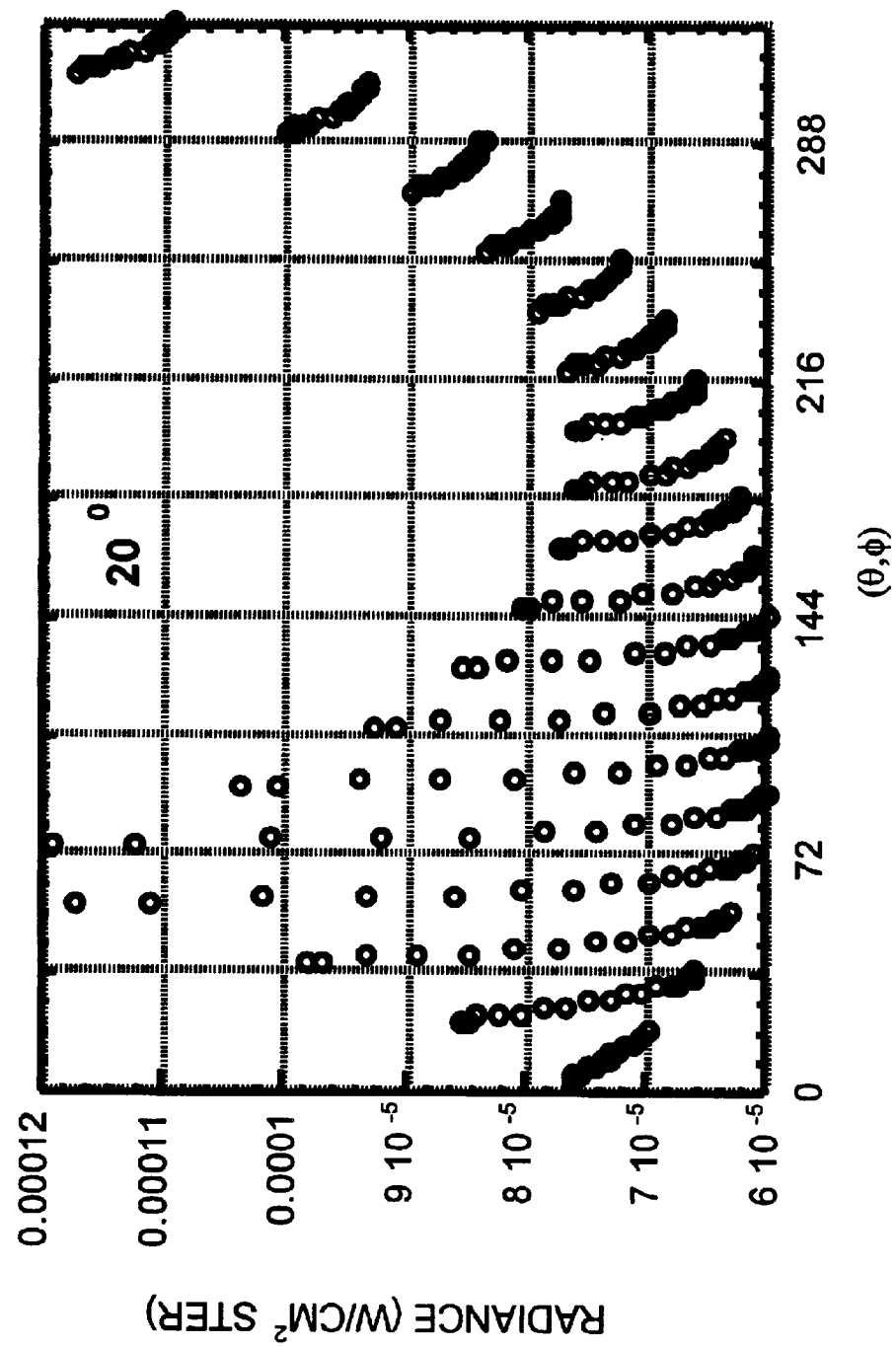
Figure 3:
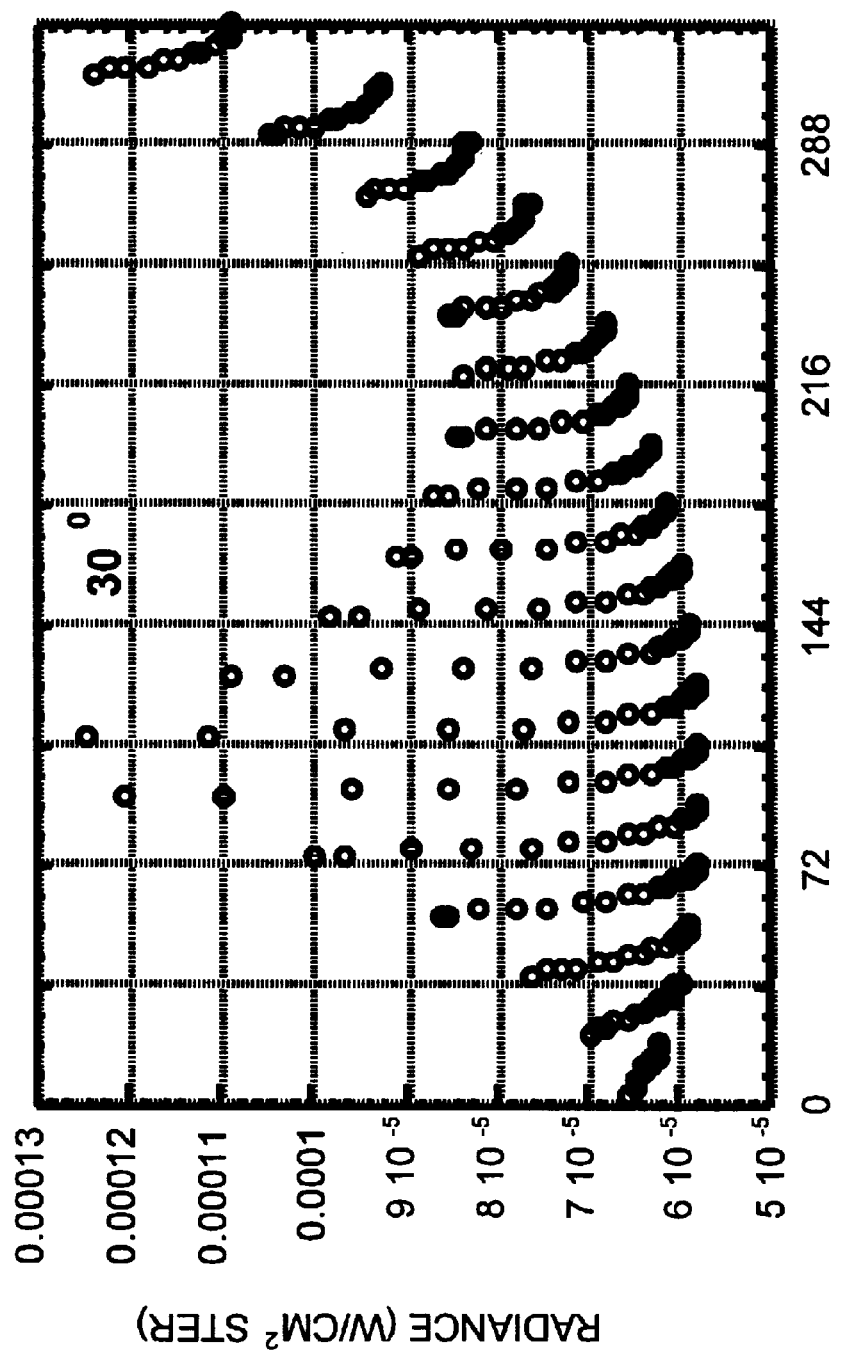
Figure 4:
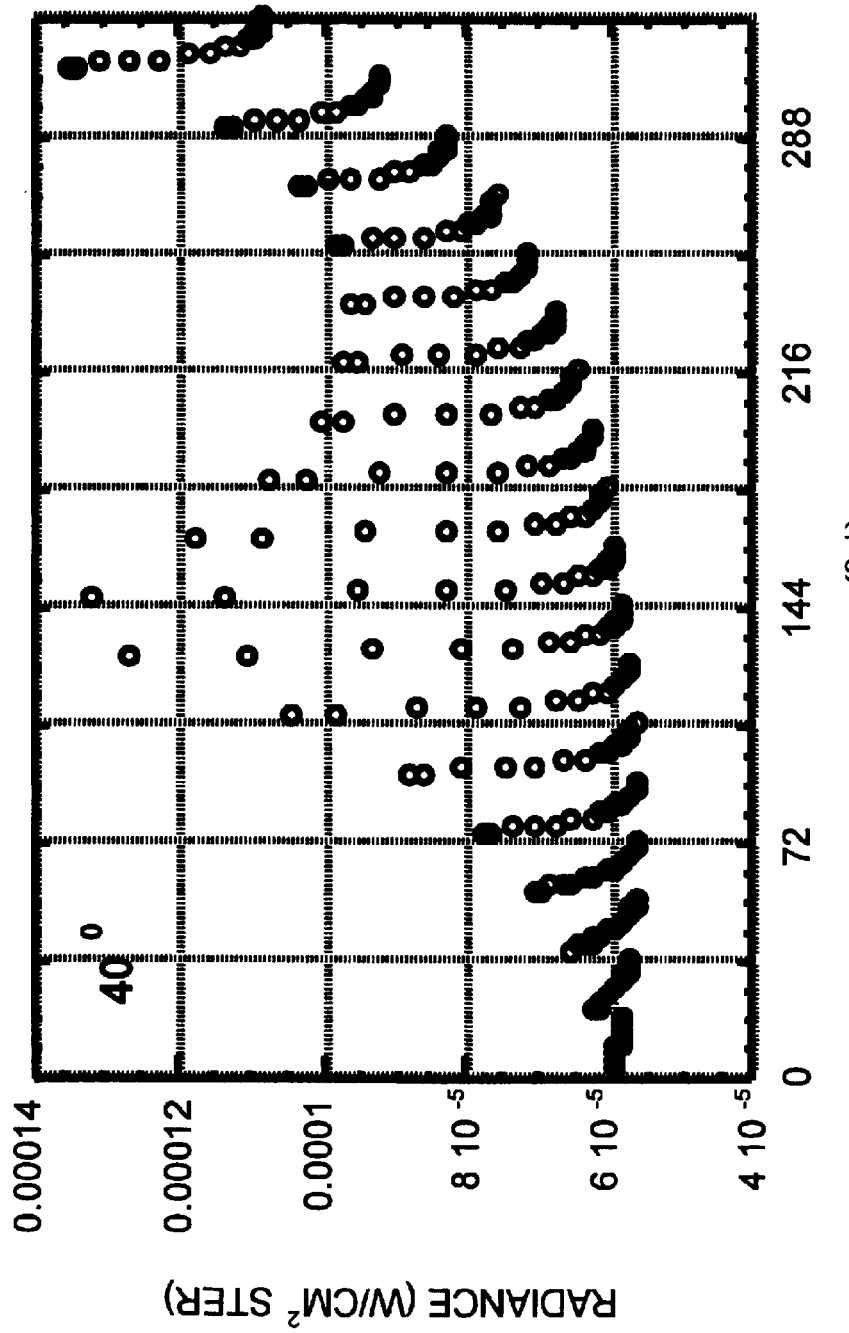
Figure 5:
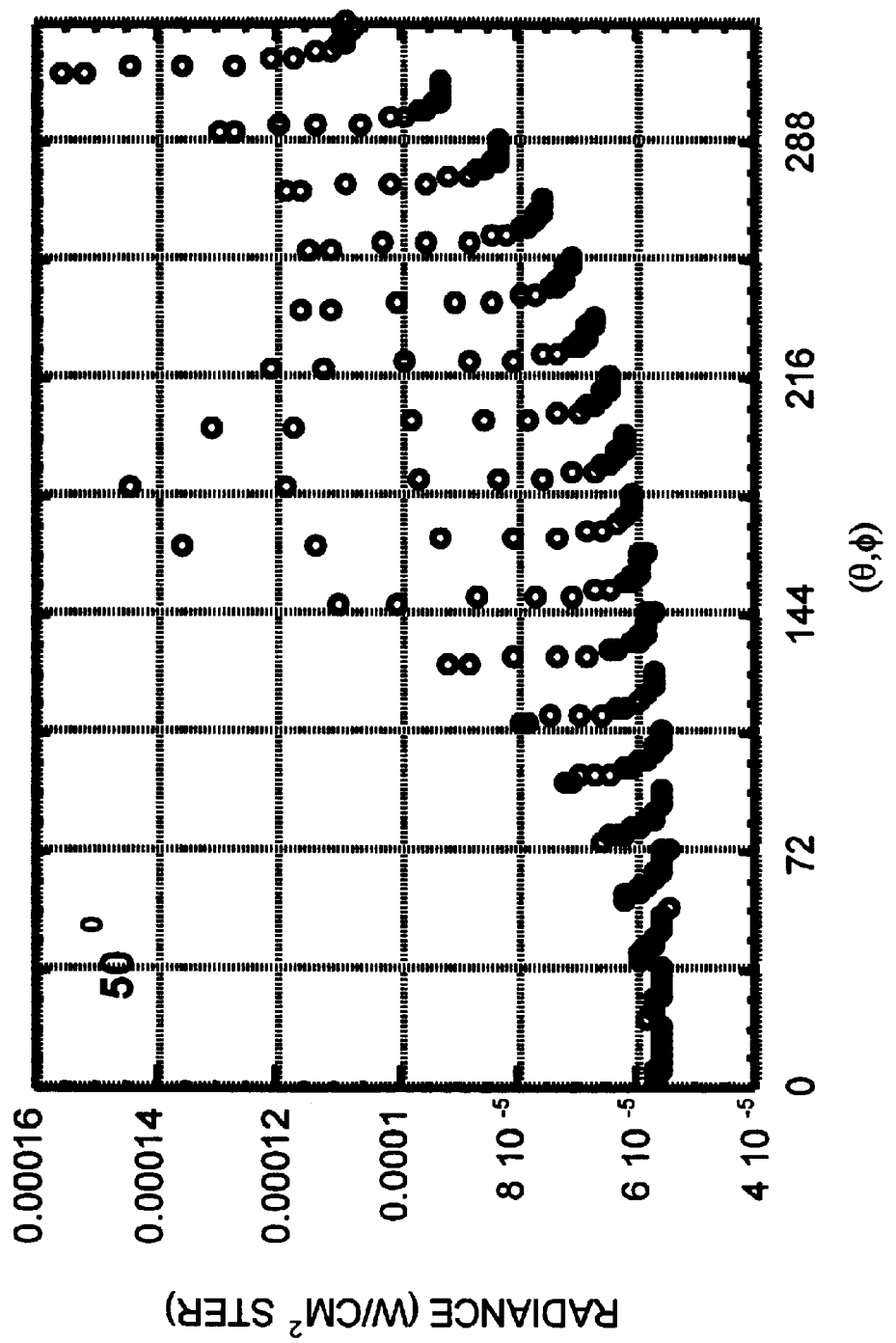
Figure 6:
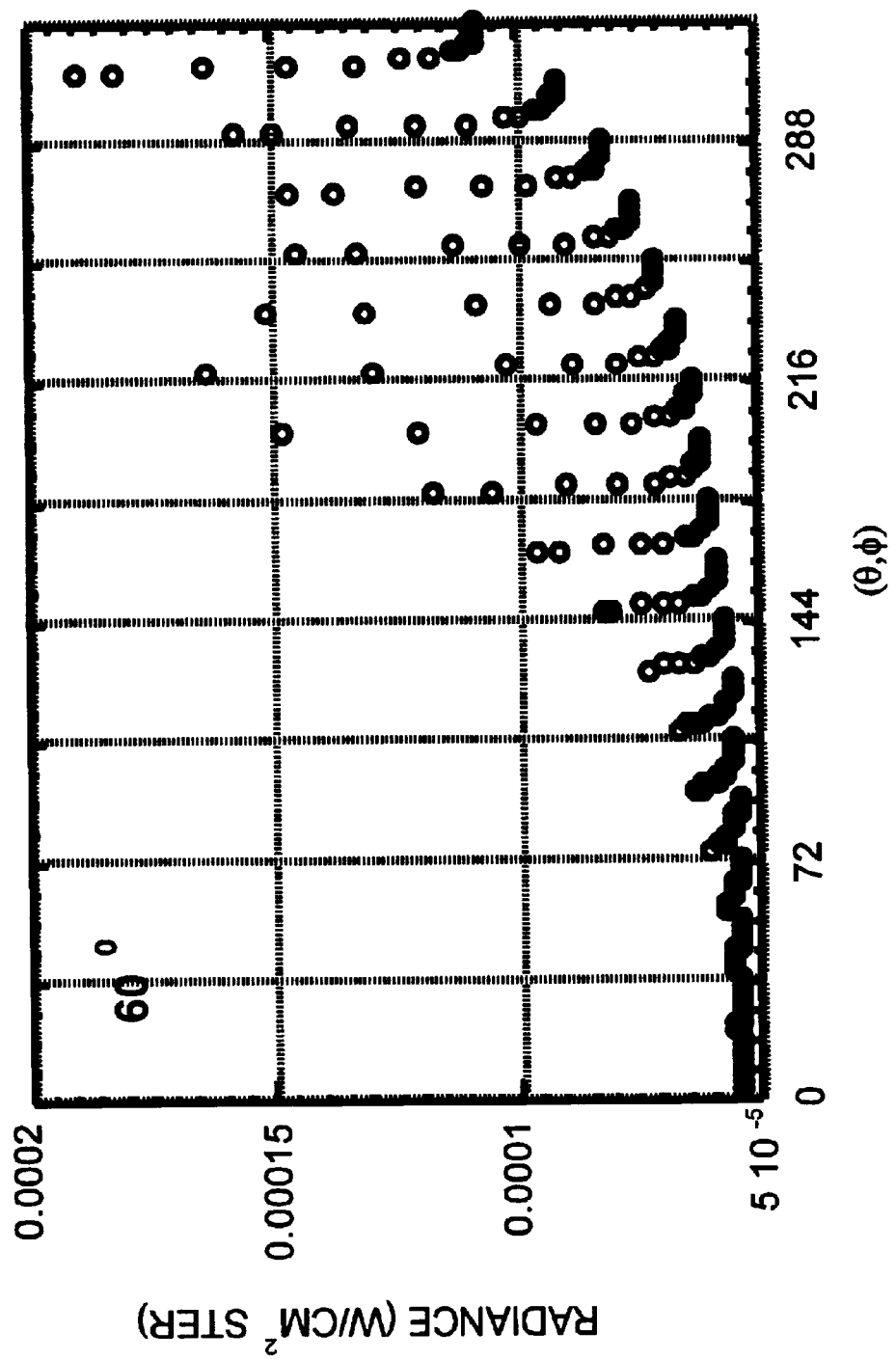
Figure 7:
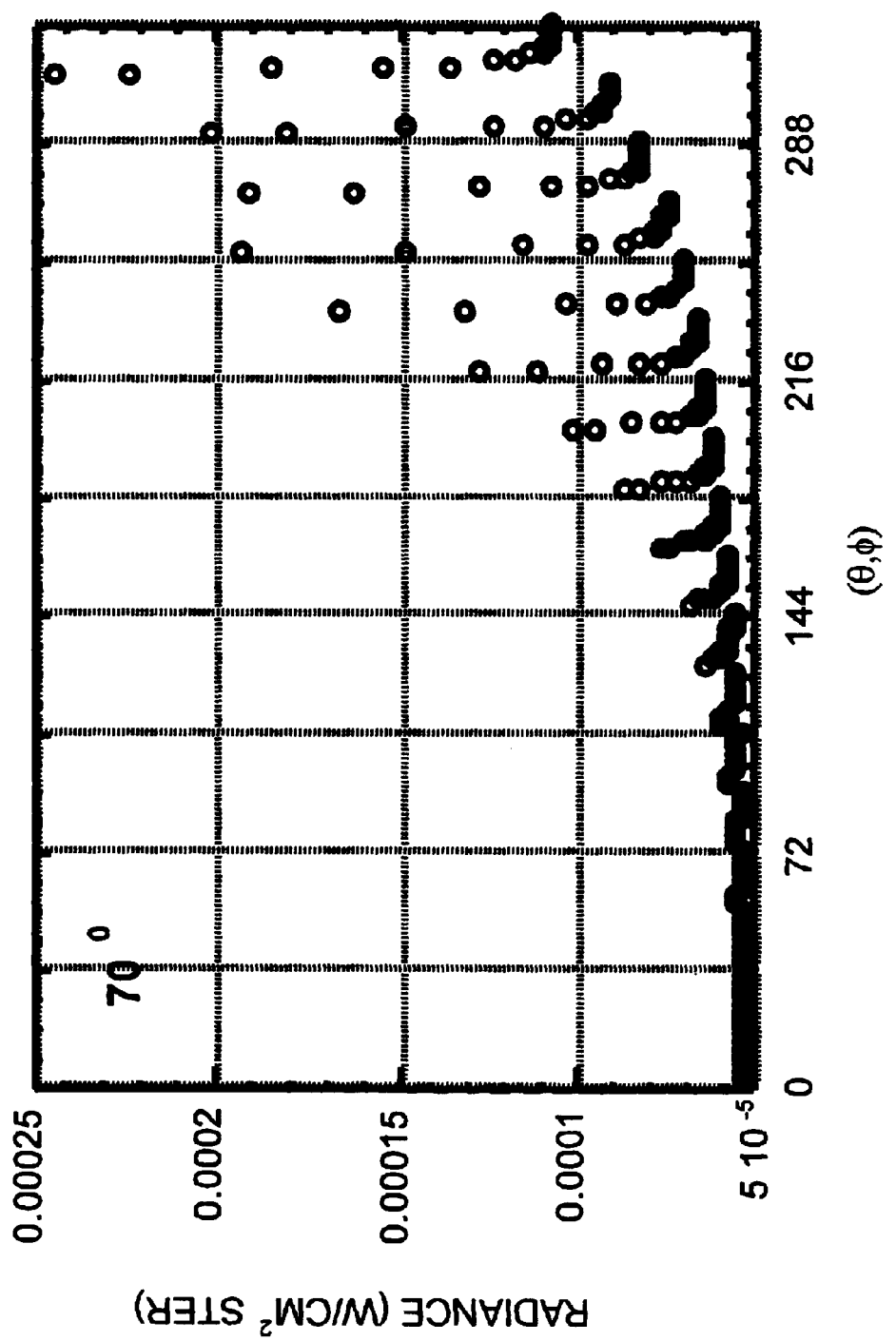
Figure 8:
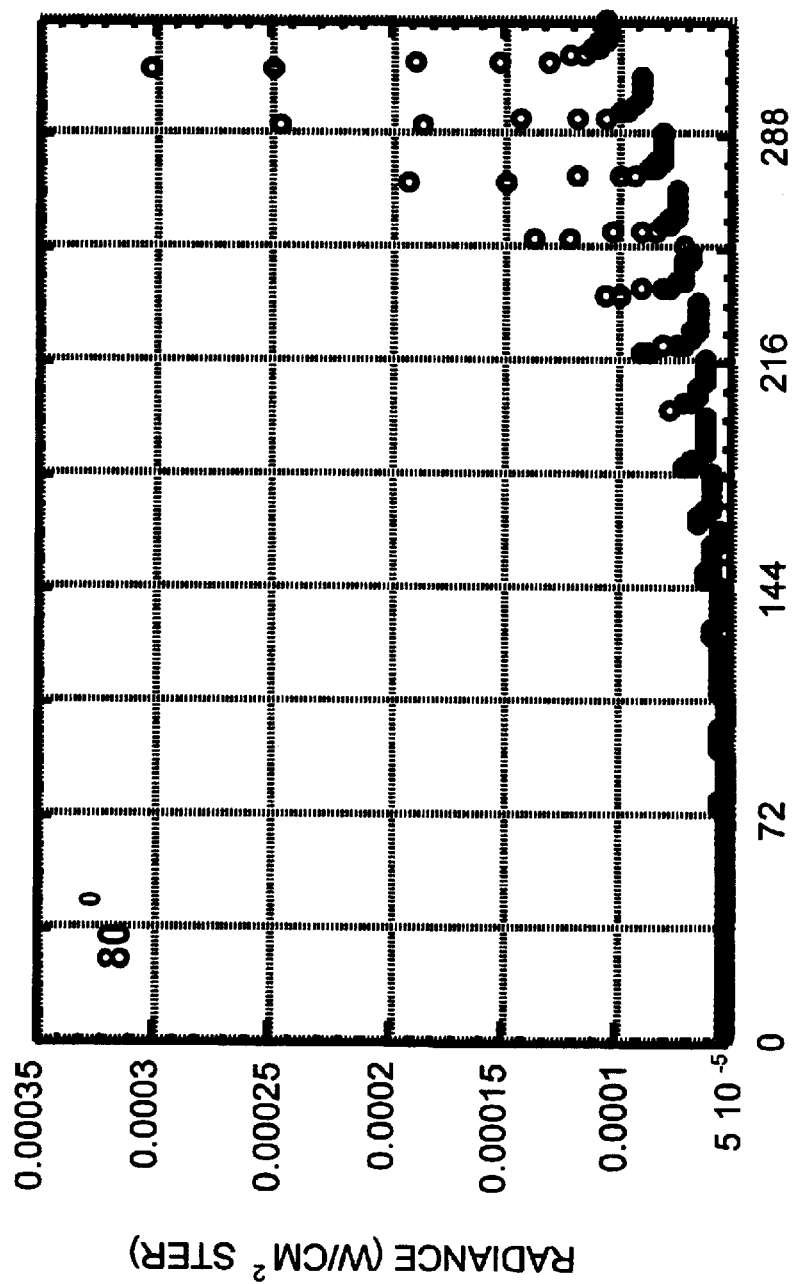

The energy source of target radiance comes from the thermal emission of the surface itself and partially reflected background of sky/sea/terrain and sun irradiance at the surface. In accordance with typical embodiments of the present invention, the BRDF is calculated numerically by taking properly chosen images of the target and its hemispheric background under (i) different geometrical viewing conditions or (ii) timely changing environmental conditions. Natural background, including the sun, is the source of illumination for the target surface. The recorded images of the target and its associated surrounding background are radiometrically calibrated against the blackbodies to get radiance from pixel values.

In accordance with the present invention, the BRDF can be determined accurately (with the help of a theoretical model such as developed by NSWCCD) by considering the images of the target surface in the selected/predetermined favorable background conditions. The inventive methodology thus represents a kind of "reverse process." The reverse process in accordance with the present invention involves performance of a (typically, large) matrix inversion. As disclosed herein, this inventive reverse process has been demonstrated numerically by the inventor. The inventive examples described herein will appropriately inform and guide the ordinarily skilled artisan so as to be capable of conducting inventive experimental measurements and engaging in inventive practice in general.

FIELD CALIBRATION

The thermal imaging radiometer responds to an effective in-band radiance from a reference blackbody radiation source. Generally, for each measurement condition, the calibration was conducted by viewing at least two different blackbodies maintained at various different temperatures. The thermal imager responds to an effective in-band radiance from the reference radiation sources, which is calculated at each reference blackbody temperature from:

$$L_{eff}(T_b) = \int \{L_\lambda(\lambda, T_b)\varepsilon_b(\lambda)\tau_a(\lambda) + L_\lambda(\lambda, T_a)[1 - \tau_a(\lambda)]\}R(\lambda)d\lambda \quad (2)$$
$$= L_b + L_{path}$$

where
$T_b$=Blackbody temperature
$T_a$=Air temperature
$L_{eff}(T_b)$=Effective in-band radiance at $T_b$
$L\lambda(\lambda, T)$=Theoretical in-band spectral radiance of a blackbody at temperature T
$\varepsilon_b(\lambda)$=Spectral emissivity of the blackbody
$\tau_a(\lambda)$=Spectral atmospheric transmission
$R(\lambda)$=Normalized spectral response
$L_b$=Theoretical blackbody in-band radiance
$L_{path}$=Path in-band radiance The first term in the integral, $L_b$, represents the self-emission of the blackbody, reduced by the blackbody emissivity and the atmospheric transmission. The second term, $L_{path}$, represents radiance from the atmospheric path between the blackbody and the sensor. $L\lambda(\lambda, T)$ is the theoretical Planck's function at temperature T. The spectral response of the thermal imagers is required in Equation (2) to calculate the effective in-band radiance of the blackbody. The spectral response of a thermal image is important in order to calculate the in-band radiance of any radiation source. The thermal imaging radiometer responds to an effective in-band radiance from a reference blackbody radiation source. The thermal imagers were characterized in the laboratory to relate the incident radiant energy of the thermal imagers to the pixel intensity level.

Each frame of the video signal is digitized with 8 bits of amplitude resolution, which means that each pixel has a range of intensities of 256 different levels. For each particular scene of interest, a defined box area was generated to read out the average apparent temperature. For the spectral atmospheric transmission, $\tau_a(\lambda)$, the MODTRAN computer model was implemented using local meteorological data or measurements to determine the effect of atmospheric transmission and path radiation on any source signature. The blackbody plates with different reference temperatures were placed side by side such that the same distance was measured from the aperture of the sensor. This distance was used in MODTRAN along with local ambient temperature and relative humidity data to compute atmospheric transmissivity in the spectral bands of interest at the time of the measurement.

A system transfer function was measured to relate an object's radiance to its pixel intensity level. The imager's numerical measure of the received and detected infrared radiation is called thermal value, which is a relatively arbitrary unit of measurement. The relationship between thermal value and received photon radiation is linear. Therefore, at each blackbody temperature the thermal value I measured from the sensor can be related to the effective in-band radiance $L_{eff}$ by the following linear equation:

$$L_{eff}=aI+b \quad (3)$$

where the constants a and b, the slope and intercept, can be determined if there are at least two reference temperatures selected for calibration measurement. Two or three reference temperatures encompassing the entire measurement range were chosen and field calibration was performed just prior to data collection in any measurement sequence. The radiance conversion function of Equation (3) was used to convert the thermal values to radiance units.

A transfer function is the mathematical relationship between the output and the input of a control system or particular component. Generally, a transfer function represents the ratio of output response to input signal. This ratio can be expressed in a mathematical statement or graph (e.g., in a frequency-response plot). Typically, for a linear system, the transfer function represents the Laplace transform of the output divided by the Laplace transform of the input under conditions of zero initial-energy storage.

TARGET AND BACKGROUND SIGNATURE

NSWCCD investigators have sought some understanding of the SYNSEA code—in particular, the theoretical models used in the SYNSEA and IR tools computer code for generating IR sea background imagery. Incorporated herein by reference is the following paper concerning the SYNSEA code: Bruce W. Ball, "SYNSEA code for generating Synthetic IR Imagery of Sea," *Society of Photo-Optical Instrumentation Engineers (SPIE) Proceedings*, Characterization, Propagation, and Simulation of Sources and Backgrounds II, held 20 Apr. 1992, Orlando, Fla., Dieter Clement et al., Eds., September 1992, Volume 1687, pp 289–298. Ball discloses the following in his abstract: "The emitted and reflected contributions to infrared sea radiance are affected by factors such as water temperature; prevailing weather conditions, wave structure, and viewing geometry. These factors are all addressed in the computer code SYNSEA, which generates synthetic IR sea background imagery. In generating a radiance value for a scene pixel, SYNSEA calculates the radiance contributions for a distribution of surface orientations, weights these contributions according to the probabilities with which the orientations will occur, and sums the weighted contributions. SYNSEA predicts a unique surface orientation distribution for each pixel based upon the IFOV and the randomness of,the surface, allowing the radiance calculations to make a smooth transition between the extremes of high and low resolution. SYNSEA has been coded in a modular fashion to facilitate modifications for integration with other codes. Although the statistics of the clutter predicted by- SYNSEA have not yet been compared to any measurements, mean radiance values predicted with SYNSEA calculations have compared well with radiometric measurements."

The sky radiance can be calculated from a suitable atmospheric transmittance/radiance program such as the SKYRAD ("SKY RADiance") code (used, e.g., by the Naval Surface Warfare Center, Carderock Division) or the MODTRAN ("MODerate resolution TRANsmittance") code (used, e.g., by the Air Force Research Laboratory). In inventive practice, it is important to validate the existing computer model by comparing the infrared radiance predicted by the code to the real IR signature measurements of the backgrounds (sky and sea) in a variety of weather conditions.

Several atmospheric transmittance/radiance software products are available to the public, notable among them being the MODTRAN code. Incorporated herein by reference are the following two U.S. patents pertaining to MODTRAN: Anderson et al. U.S. Pat. No. 5,884,226 issued 16 Mar. 1999; Abreu et al. U.S. Pat. No. 5,315,513 issued 24 May 1994. Also incorporated herein by reference is the following SPIE paper concerning MODTRAN: P. K. Acharya, A. Berk, G. P. Anderson, N. F. Larsen, S-Chee Tsay and K. H. Stamnes, "MODTRAN4: Multiple Scattering and Bi-Directional Reflectance Distribution Function (BRDF) Upgrades to MODTRAN," *Society of Photo-Optical Instrumentation Engineers (SPIE) Proceedings*, Optical Spectroscopic Techniques and Instrumentation for Atmospheric and Space Research III, held July 1999, Allen M. Larar, Ed., October 1999, Volume 3756, pp 354–362. An electronic reprint of Acharya et al. is available, as well, at the Spectral Sciences, Inc. website (http://www.spectral.com/) at http://www.spectral.com/sr115.pdf.

The infrared radiation emitted or reflected by the target has to be attenuated by the atmosphere before reaching the sensor. The atmosphere also emits radiation to be received by the sensor. Therefore, knowing the exact atmospheric condition is one of the crucial factors involved in FLIR ("Forward-Looking InfiaRed") performance. The constituents of the atmosphere such as water vapor, carbon dioxide and ozone are the principal molecular infrared absorbers. In addition, suspended particulate matter such as smoke, dust, and water droplets in the form of clouds, fog and haze scatter and absorb the radiation. For each measurement, the atmospheric attenuation as a function of range for each waveband was calculated by the U.S. Navy using the environmental data and using MODTRAN.

The U.S. Navy performed experimental measurements, in accordance with the present invention, of temporally and spatially dependent target and background signatures using an imaging radiometer in the thermal IR and visible regions. These experimental measurements of various ship's signatures were conducted by NSWCCD for the MARK V, the DDG57, the HIDDENSEE and the PALE ALE, and reports associated with such testing have been made publicly available. In such measurements, the inventive practitioner intends to use the "fish eye" lens of the thermal imaging radiometer to measure, directly and accurately, the realistic hemispheric background signature in all azimuth and elevation angles.

The effective in-band apparent radiance from an object with temperature $T_0$ is given theoretically by:

$$L_{\mathit{eff}}(T_0) = \int \{[L_{80}(\lambda, T_0)\epsilon_0(\lambda) + \Phi_s \rho_{0(\lambda)}\tau_a(\lambda)]\}R(\lambda)d\lambda + L_{\mathit{path}} \qquad (4)$$

where $L\lambda(\lambda, T_0)$ = Effective in-band radiance at $T_0$ $\epsilon_0(\lambda)$ = spectral emissivity of the target $\rho_0(\lambda)$ = spectral reflectivity of the target $\Phi_s(\lambda)$ = spectral solar radiation The contribution to the target and background (sky/sea) signature comes from direct emission and reflection. In Equation (4), the first term in the integral represents the object's self-emission radiation and the second term represents its reflected solar radiation from the object. The term $L_{\mathit{path}}$, which was defined in Equation (2), represents the atmospheric path radiance between target and imager. The source radiance value contains the object's self-emission and reflected solar radiation. To determine the source radiance, the path radiance represented by the second term, $L_{\mathit{path}}$, was subtracted from the apparent radiance signature. Finally, the source radiance values, L, were determined by taking into account the atmospheric transmission losses:

$$L = (L_{\mathit{eff}} - L_{\mathit{path}})/\overline{\tau}_a \qquad (5)$$

where the average in-band atmospheric transmission value of Equation (6), below, is used:

$$\overline{\tau_a} = (\lambda_2 - \lambda_1)^{-1} \int_{\lambda_1}^{\lambda_2} \tau_a(\lambda) d\lambda \qquad (6)$$

For the case considered here, the ship is the target. The apparent contrast temperature of the ship, defined by the apparent temperature difference between the ship and background, is related to source contrast temperature by:

$$(L(\text{ship}) - L(\text{background})) = (L_{\text{eff}}(\text{ship}) - L_{\text{eff}}(\text{background}))\overline{\tau_a} \qquad (7)$$

Equation (7) allows us to convert the contrast apparent temperature to contrast source temperature. The results of measuring apparent ship-background temperature difference can be used to calculate the source contrast temperature by taking into account the atmospheric attenuation. As a result, it enables us to predict the apparent contrast temperature under various weather conditions, for example by effecting a histogram corresponding to a region covering the target. The average apparent radiance $\overline{L_{\text{eff}}}$ can be obtained from the following equation:

$$\Sigma L_{\text{eff}\,i} n_i = \overline{L_{\text{eff}}} \Sigma n_i \qquad (8)$$

where the lefthand side is expressed as a summation because the radiance map is discrete and has its own value for each pixel, $L_{\text{eff}}$ is the mean radiance, and $n_i$ is the number of pixels that have a radiance value between $L_{\text{eff}}$ and $(L_{\text{eff}} + dL_{\text{eff}})$. Equation (8) gives the average apparent temperature of the target from its histogram.

BI-DIRECTIONAL REFLECTANCE DISTRIBUTION FUNCTION

For the source radiance of a surface in the normal direction, the BRDF in the normal direction to the surface will determine the reflecting contribution of the source radiance due to its hemispheric background. Let us assume that a plane surface lies on the top of the earth's surface in high ground area so that the plane surface faces nothing but the whole sky, the sky dome thereby becoming the illumination source. The apparent spectral radiance of a target can be expressed by:

$$L = \tau(R)\left[(1-\rho)L_b(T_0) + \int_0^{2\pi} d\phi, \right. \qquad (9)$$

$$\left. \int_0^{\pi/2} d\theta B(\theta, \phi) L_{bg}(\theta, \phi) \cos\theta \sin\theta \right] + L_{path}$$

where the BRDF is related to the hemispheric reflectance by:

$$\rho = \int_0^{2\pi} d\phi \int_0^{\pi/2} d\theta B(\theta, \phi) \cos\theta \sin\theta \qquad (10)$$

The source radiance of the sky including the sun is aiming toward the surface of the target from every hemispheric direction. We can make the hemispheric sky discrete in the zenith and azimuth directions so that each angle pair of $(\theta,\phi)$ represents the radiation source of the sector covered by $\delta\theta$ and $\delta\phi$. The sky radiance can be calculated in the zenith direction between 0 and 90 degrees and in the azimuth direction between 0 and 360 degrees. The values of sky radiance and solar irradiance for any environmental condition can be measured directly or calculated by using MODTRAN-4 code. For any day of the year, we record the images of the surface and its hemispheric sky when the sun's zenith angle varies from 5° to 85° with 5° apart.

The typical sky radiance for mid-wave band (3–5 $\mu$m) calculated from MODTRAN for the sun's zenith angle from 10° to 80° with 10° apart is shown in FIG. 1 through FIG. 8. The division angle of 5° is taken as $\theta$ varies from 0° to 90° and 10° as $\phi$ varies from 0° of facing the sun to 180°. The azimuth symmetry of the sky radiance with respect to the sun is expected in the MODTRAN computer code. The radiance data contain sky radiance tabulated at the values of the zenith and azimuth angles which will cover the sky.

Figure 9:
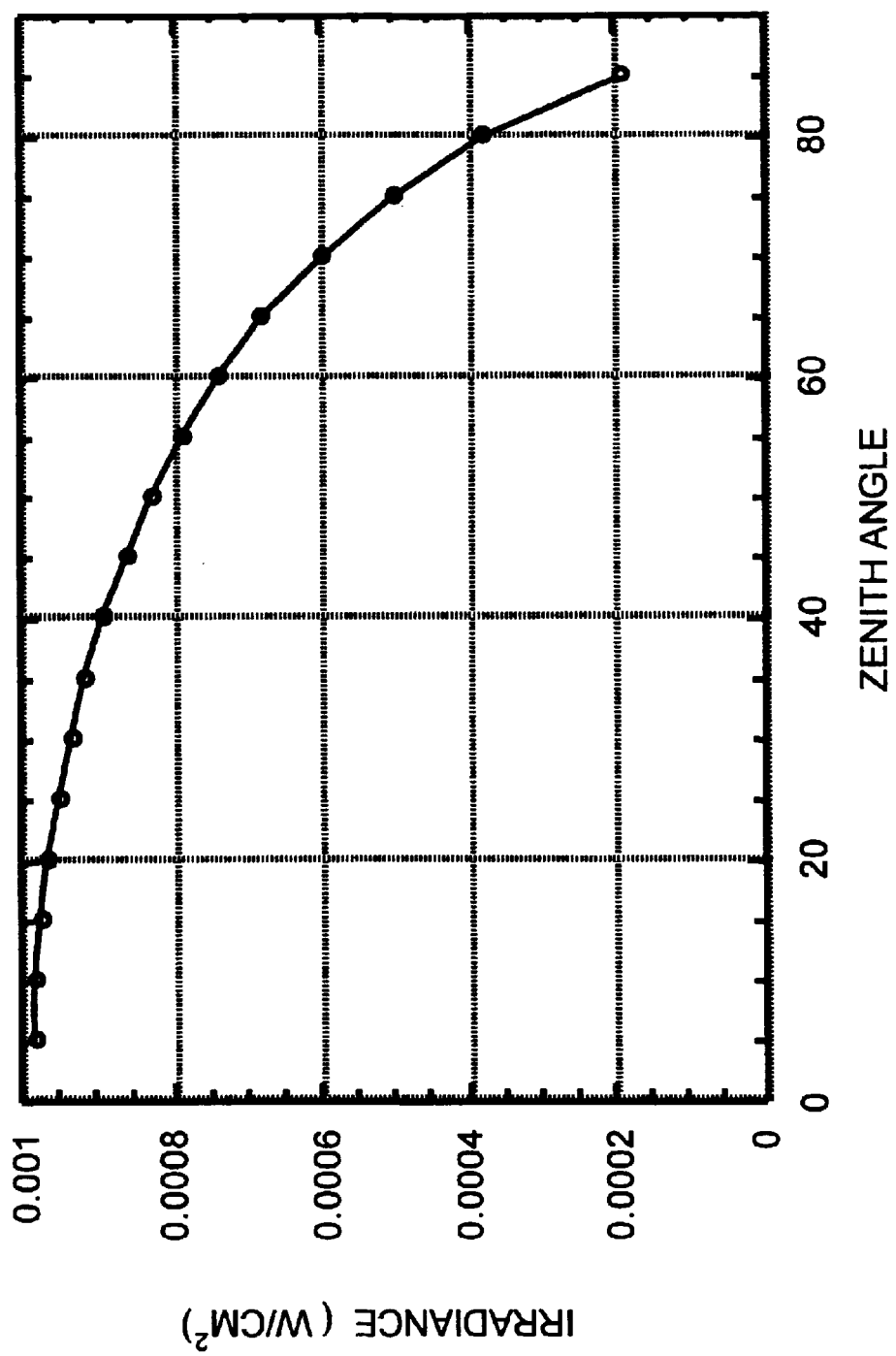
FIG. 9 is a graphical representation of the solar irradiance calculated as a function of zenith angle, in accordance with an embodiment of the present invention.

The spectral atmospheric path radiance and spectral transmittance from the observer to the target are obtained using MODTRAN along with the prevailing meteorological data. The solar irradiance term is an integral over only the solar disk. The solar irradiance calculated is shown in FIG. 9 as a function of zenith angle. Solar radiance is added to sky radiance if sky point falls within solar disk.

Figure 10:
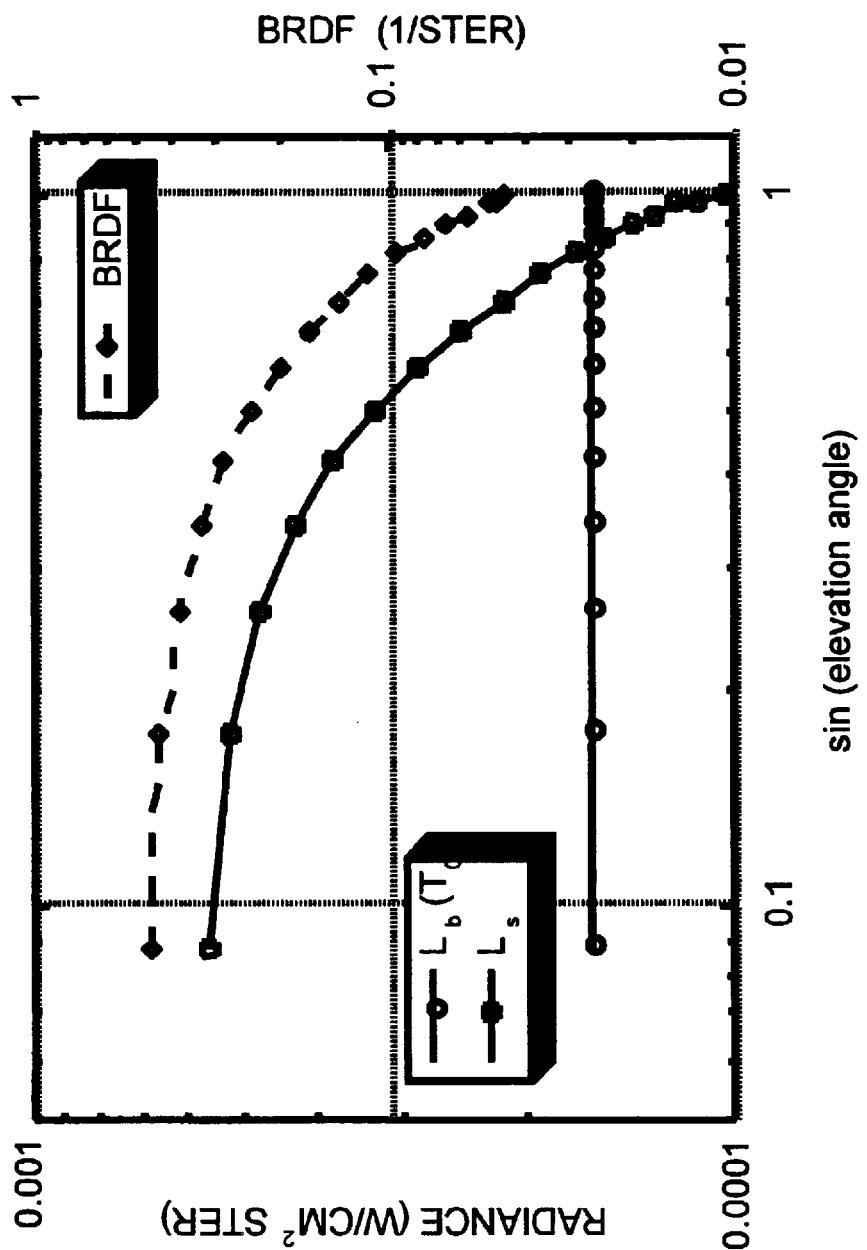
FIG. 10 through FIG. 13 are graphical representations of the BRDF obtained from the assumed source radiance, in accordance with an embodiment of the present invention.
Figure 11:
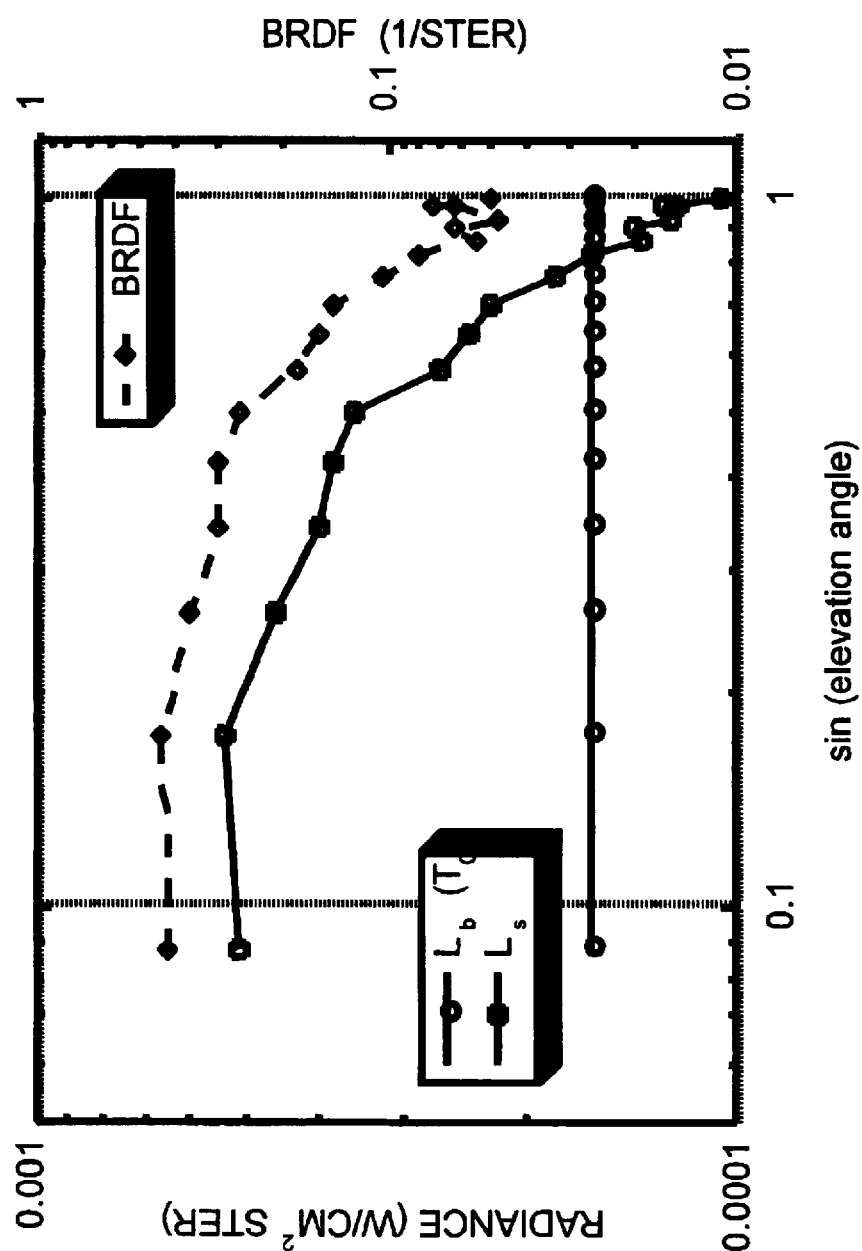
Figure 12:
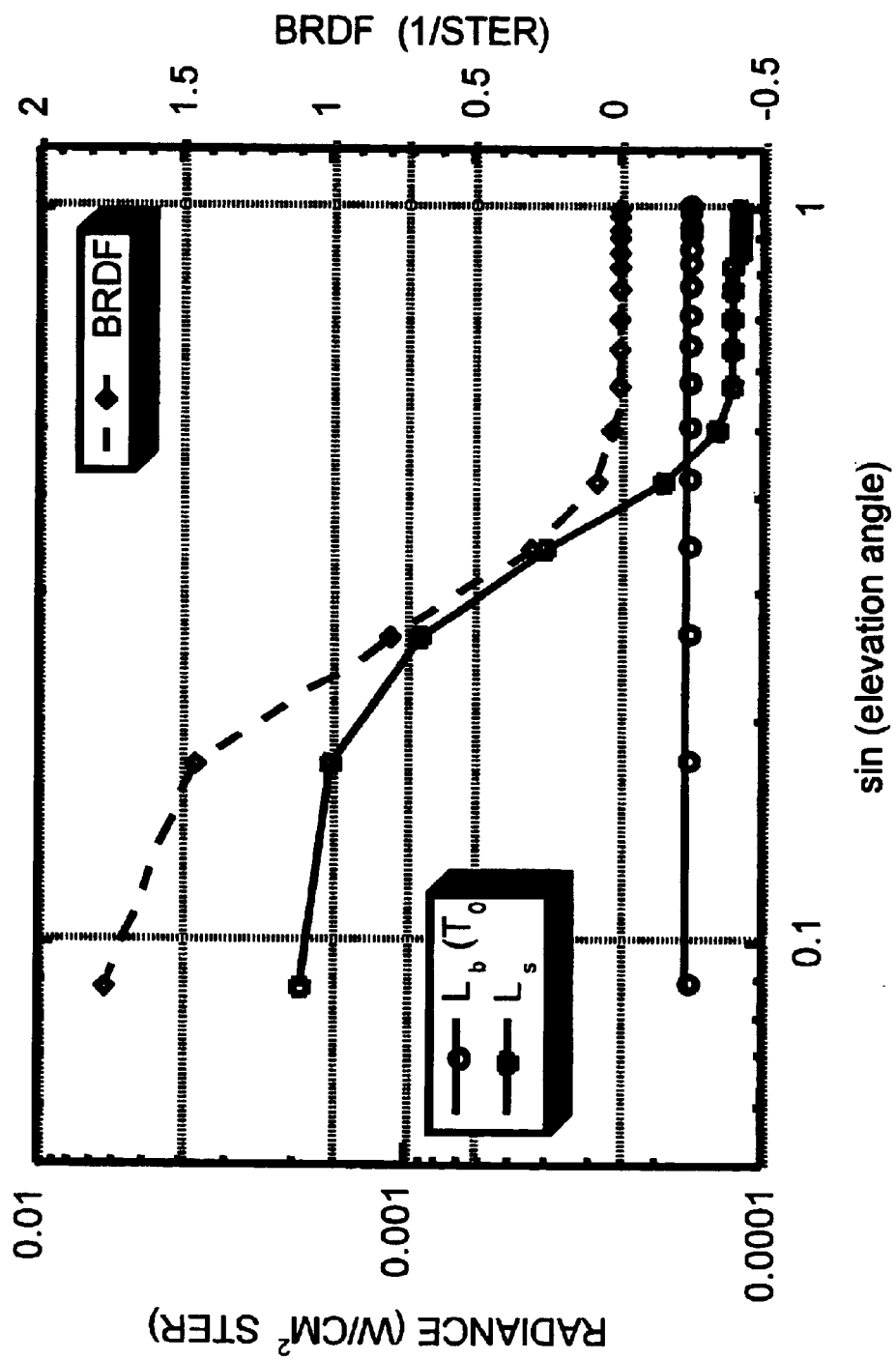
Figure 13:
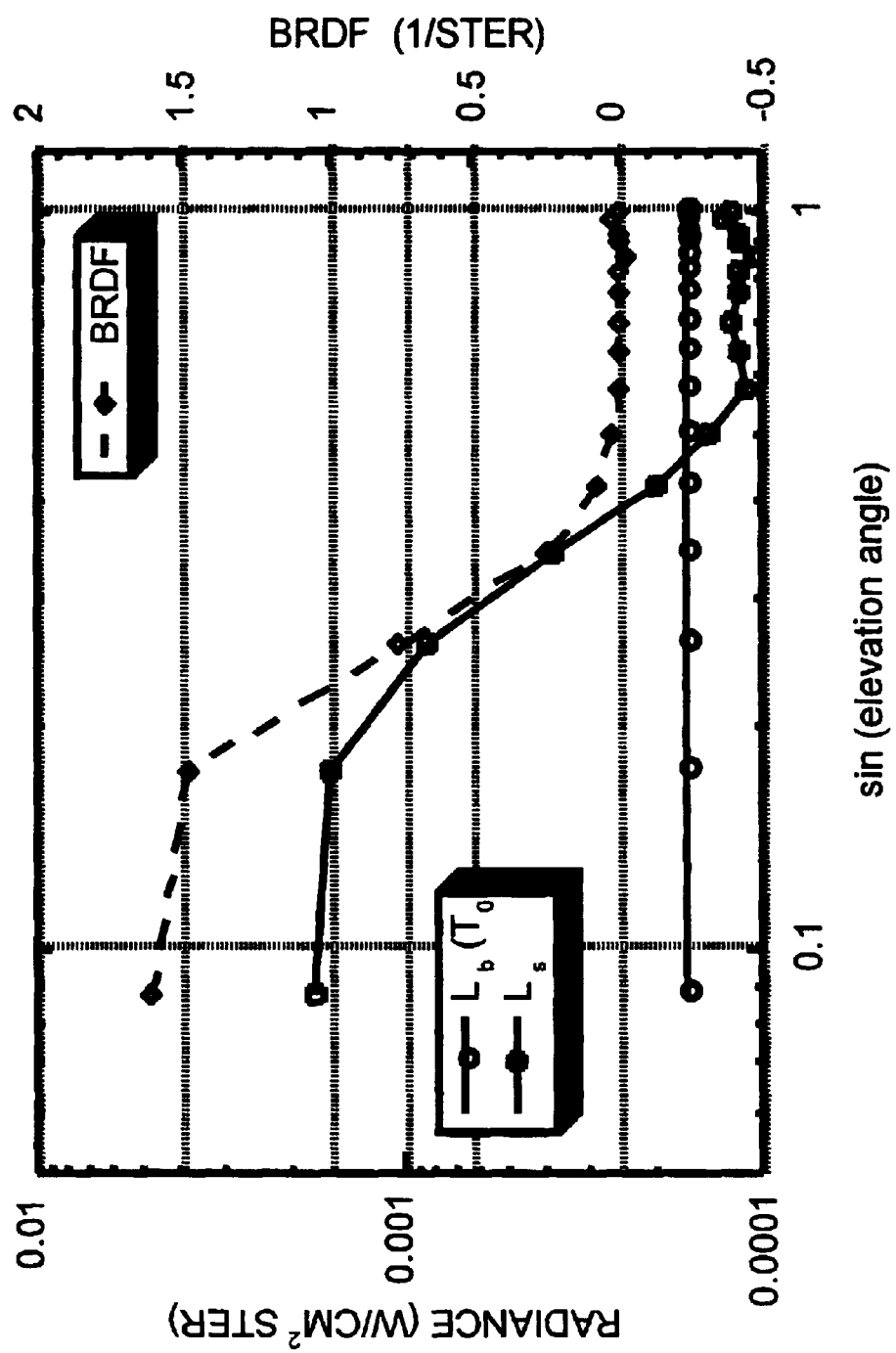

With reference to FIG. 10 through FIG. 13, let us further assume for simplicity's sake that the BRDF is symmetrical in the azimuth direction. The sky radiance is integrated in the azimuth direction for each zenith angle. Under the pre-described environmental conditions, if the zenith angle dependent source radiance of the surface in the normal direction is measurable within the accuracy of the radiometer, then the BRDF can be calculated numerically by inverting a large matrix. A few examples are illustrated in FIG. 10 through FIG. 13. FIG. 10 shows the BRDF obtained from the assumed source radiance as a function of $\sin(\theta)$. The temperature of the target was assumed constant for convenience. FIG. 11 is the case while the source radiance has a random 10% error. Another example, similar to the example shown in FIG. 10 and FIG. 11, is shown in FIG. 12 and FIG. 13.

The numerical examples shown in FIG. 10 through FIG. 13 represent the simplest mode of inventive practice, wherein the. BRDF of an object of interest is isotropic, and wherein the incident direction of the assumed source (e.g., sky) radiance is normal to the object of interest. In the light of the instant disclosure, the ordinarily skilled artisan will be capable of practicing the present invention in a variety of BRDF determination applications, ranging from the simplest to the most complicated cases.

Performing matrix inversion is not unlike solving a set of simultaneous equations. Basically, matrix inversion involves finding the "inverse matrix" in association with an original matrix such that the product of the inverse matrix and the original matrix equals I, where I is the so-called "identity matrix" or "unit matrix." In other words, the inverse of a nonsingular matrix A is the matrix $A^{-1}$, where $(A)(A^{-1}) = (A^{-1})(A) = I$. Thus, matrix inversion involves the determination, for a given matrix A, of its inverse matrix $A^{-1}$ such that $(A)(A^{-1}) = (A^{-1})(A) = I$. Various computer programs are available to the public for performing matrix inversion. Two typical matrix inversion techniques, well known to ordinarily skilled people in the pertinent arts, are (i) matrix inversion by elimination and (ii) matrix inversion by using the adjoint matrix. Generally speaking, matrix inversion by elimination tends to be more suitable for moderate and large matrices, while matrix inversion by using the adjoint matrix tends to be more suitable for small matrices. Typically according to inversion by elimination, a form of Gaussian elimination is effected for computing the inverse matrix. Typically according to inversion by using the adjoint matrix, the inverse matrix is computed explicitly through calculating the adjoint matrix from cofactors and scaling by the determinant. See, e.g., the following textbook, incorporated herein by reference: Reiner, Irving, *Introduction to Matrix Theory and Linear Algebra*, Holt Rinehart Winston, N.Y., 1971.

The atmospheric attenuation was taken into consideration in the calculation of the source temperature of the target, so that the signature prediction could be made for different weather conditions if the background signature were known. Furthermore, the radiance from the sea surface and the sky can be obtained from the spectral radiometer. The source radiance signature contributed by reflection can be determined.

In inventive practice, the influence of surface reflectance on the target signature can be assessed. Every target surface has its own unique BRDF which determines the reflected portion of radiance from the surrounding background. For instance, for various parts of the ship, any combination of the following factors can introduce many variations for the BRDF: (i) the coating thickness; (ii) the surface roughness; (iii) the optical constants of the coating material; and/or, (iv) the optical constants of the substrate. The signature control can be optimized for the purpose of continuous signature-matching of the target with its changing background and the spatial signature variation reduction of the ship for the countermeasure against target detection and discrimination by parts.

In inventive practice, since the natural background is the source of illumination, it can be either (i) temporally (timely) different/dependent or (ii) spatially (geometrically) different/dependent. The main requirement in this regard is that the variation of the background give sufficient information for the measurement to decompose the source radiance to BRDF. Therefore, the choice of the background is highly dependent on the variation of the BRDF. With the help of the theoretical model in accordance with the present invention, it is much easier to choose the necessary and appropriate background.

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. A radiance-related physical property determination method comprising:

generating plural distinguishable images each being characterized by plural pixels, said generating being effected using an imaging device, each said image including a target and at least a portion of the natural hemispheric background, the atmospheric path between said target and said imaging device being characterized by path radiance, said natural hemispheric background being characterized by a hemispheric background radiance that illuminates said target, said hemispheric background radiance aiming toward the surface of said target from every hemispheric direction, said target being characterized by a target radiance and a target emission, said target radiance relation to the combination including said hemispheric background radiance, said target emission, and said path radiance;

determining said target radiance and said hemispheric background radiance that correspond to each said image, each said determination being made with respect to a said image based on pixel intensities associated with the thermal character of said image, wherein said hemispheric background radiance varies in accordance with zenith angles $\theta$ and azimuth angles $\phi$, said natural hemispheric background being characterized by said zenith angles $\theta$ and said azimuth angles $\phi$, said zenith angles $\theta$ ranging between zero and 90 degrees said azimuth angles $\phi$ ranging between zero degrees and 360 degrees; and based on said determinations corresponding to said images, calculating a bi-directional reflectance distribution function of said target;

wherein said calculating of said bi-directional reflectance distribution function includes effecting mathematical matrix inversion to obtain said bi-directional reflectance distribution function;

wherein said mathematical matrix inversion is based on plural said relationships between said target radiance and said combination including said hemispheric background radiance, said target emission, and said path radiance;

wherein each said image has at least one said relationship associated therewith for effecting said mathematical matrix inversion;

wherein said mathematical matrix inversion is effected in relation to plural said images;

wherein said relationship between said target radiance and said combination is mathematically expressed as $$L = \tau(R)\left[(1-\rho)L_b(T_0) + \int_0^{2\pi} d\phi \int_0^{\pi/2} d\theta B(\theta, \phi)L_{bg}(\theta, \phi)\cos\theta\sin\theta\right] + L_{path}$$

wherein:

the term $(1-\rho)L_b(T_0)$ corresponds to said target emission;

the term $$\int_0^{2\pi} d\phi \int_0^{\pi/2} d\theta B(\theta, \phi)L_{bg}(\theta, \phi)\cos\theta\sin\theta$$

corresponds to said hemispheric background radiance;

L is said target radiance;

$\tau(R)$ is the hemispheric atmospheric transmission;

$L_b$ is the blackbody radiance;

$T_\theta$ is the temperature of said target;

$L_{bg}$ is the hemispheric background radiance;

$L_{path}$ is said path radiance;

$\Phi$ is said azimuth angle;

$\theta$ is said zenith angle;

B is said bi-directional reflectance distribution function;

$\rho$ is the reflectance of said natural hemispheric background;

$$\rho = \int_0^{2\pi} d\phi \int_0^{\pi/2} d\theta B(\theta, \phi)\cos\theta\sin\theta.$$

2. The radiance-related physical property determination method defined in claim 1, wherein said images are each at least one of:

geometrically distinguishable; and temporally distinguishable.

3. The radiance-related physical property determination method defined in claim 1, wherein said hemispheric radiance includes sky radiance and solar irradiance.

4. The radiance-related physical property determination method defined in claim 1, wherein each said image includes a target and a portion of said natural hemispheric background, and wherein said determining values for said hemispheric radiance is based on pixel intensities of pixels characterizing said portion of said natural hemispheric background.

5. The radiance-related physical property determination method defined in claim 1, wherein each said image includes a target and at least substantially the entire said natural hemispheric background, and wherein said determining values for said hemispheric radiance is based on pixel intensities of pixels characterizing said at least substantially the entire said natural hemispheric background.

6. The radiance-related physical property determination method defined in claim 5, wherein said imaging device includes a fish eye lens for capturing said at least substantially the entire said natural hemispheric background in a said image.

7. A method of determining the bi-directional reflectance distribution function of an object, said method comprising:
    recording a plurality of different images containing pixels, each said image being of said object in combination with at least a portion of the natural hemispheric background that illuminates said object, said recoding including using an imaging device for placement relative to said object so as to describe a path between said imaging device and said object;
    for each said image, ascertaining said object's radiance and said background's radiance, said pixels being indicative of said object's radiance and said background's radiance; and
    based on said ascertained radiances, performing calculation including matrix inversion calculation so as to obtain said bi-directional reflectance distribution function;
    wherein each said imager is considered in terms of at least one relationship among said object's radiance, said background's radiance, said object's emission, and said path's radiance;
    wherein said matrix inversion is performed with respect to plural said relationships;
    wherein said matrix inversion is performed with respect to plural said images;
    wherein said relationship among said object's radiance, said background's radiance, said object's emission, and said path's radiance is mathematically expressed as $$L = \tau(R)\left[(1-\rho)L_b(T_0) + \int_0^{2\pi} d\phi \int_0^{\pi/2} d\theta B(\theta, \phi)L_{bg}(\theta, \phi)\cos\theta\sin\theta\right] + L_{path}$$

wherein:
    the term $(1-\rho)L_b(T_0)$ corresponds to said object's emission;

the term $$\int_0^{2\pi} d\phi \int_0^{\pi/2} d\theta B(\theta, \phi)L_{bg}(\theta, \phi)\cos\theta\sin\theta$$

corresponds to said background's radiance;
    L is said object's radiance;
    $\tau(R)$ is the hemispheric transmission;
    $L_b$ is the blackbody's radiance;
    $T_\theta$ is the temperature of said object;
    $L_{bg}$ is said background's radiance;
    $L_{path}$ is said path's radiance;
    $\Phi$ is the azimuth angle;
    $\theta$ is the zenith angle;
    B is said bi-directional reflectance distribution function;
    $\rho$ is the reflectance of said natural hemispheric background;

$$\rho = \int_0^{2\pi} d\phi \int_0^{\pi/2} d\theta B(\theta, \phi)\cos\theta\sin\theta.$$

8. The method of determining the bi-directional reflectance distribution function according to claim 7, wherein the differentiation between said images is based on temporal variations, said images being recorded at different times.

9. The method of determining the bi-directional reflectance distribution function according to claim 7, wherein the differentiation between said images is based on spatial variation, said images being recorded at different locations.

10. The method of determining the bi-directional reflectance distribution function according to claim 7, wherein said imaging device is a thermal imaging device, and wherein in each said image said pixels are indicative of said object's radiance and said background's radiance by virtue of pixel intensity levels associated with thermal properties of said image.

11. The method of determining the bi-directional reflectance distribution function according to claim 10, wherein, for each said image, said ascertaining of said object's radiance and said background's radiance includes:
    calibrating said thermal imaging device against theoretical blackbody radiation using measured incident radiation; and
    performing calculation including transfer function calculation so as to relate said pixel intensity levels to said object's radiance and said background's radiance.

12. The method of determining the bi-directional reflectance distribution function according to claim 10, wherein said thermal imaging device includes a radiometer.

* * * * *